US012594050B2

(12) United States Patent (10) Patent No.: US 12,594,050 B2
Fukutsuka et al. (45) Date of Patent: Apr. 7, 2026

(54) WHEEZE DETECTION DEVICE

(71) Applicant: OMRON HEALTHCARE Co., Ltd., Kyoto (JP)

(72) Inventors: Masayuki Fukutsuka, Kyoto (JP); Katsuyoshi Morita, Kyoto (JP); Hiroshi Ogawa, Kyoto (JP); Seiji Fukunaga, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 868 days.

(21) Appl. No.: 17/934,391

(22) Filed: Sep. 22, 2022

(65) Prior Publication Data

US 2023/0019623 A1      Jan. 19, 2023

Related U.S. Application Data

(63) Continuation of application No. PCT/JP2021/008091, filed on Mar. 3, 2021.

(30) Foreign Application Priority Data

Mar. 27, 2020    (JP) ................................. 2020-057186

(51) Int. Cl.
   *A61B 7/00*          (2006.01)
   *A61B 7/04*          (2006.01)
(52) U.S. Cl.
   CPC ............... *A61B 7/003* (2013.01); *A61B 7/04* (2013.01); *A61B 2562/028* (2013.01)
(58) Field of Classification Search
   CPC ...... A61B 7/003; A61B 7/04; A61B 2562/028
   See application file for complete search history.

(56) References Cited

U.S. PATENT DOCUMENTS

2003/0127282 A1    7/2003  Lee et al.
2004/0068194 A1*   4/2004  Johnson ............... A61B 5/0002
                                                  379/38

(Continued)

FOREIGN PATENT DOCUMENTS

CN        1431398 A     7/2003
CN      206303909 U     7/2017

(Continued)

OTHER PUBLICATIONS

Microfilm of the specification and drawings annexed to the request of Japanese Utility Model Application No. 6388/1972 (Laid-open No. 84485/1973) (Primo KK) Oct. 13, 1973, description, p. 2, lines 1-12, all drawings.

(Continued)

*Primary Examiner* — Andrey Shostak
(74) *Attorney, Agent, or Firm* — Birch, Stewart, Kolasch & Birch, LLP

(57) ABSTRACT

A wheeze detection device that allows suppressing a noise and improving detection accuracy of wheezing. The device includes a first microphone configured by a MEMS microphone, a space-forming member (a first housing, an O-ring, a flexible circuit board, and a second housing) forming an accommodation space that accommodates the first microphone, and a housing cover that forms a pressure receiving unit that closes the accommodation space and receives a pressure from a body surface. The space-forming member has a hole portion connected to an atmosphere. The accommodation space is connected to the atmosphere via the hole portion. The hole portion includes branch portions to between a groove and a terminal and two branched hole portions branched at each branch portion from a side of the groove. One branched hole portion among the two branched hole portions is connected to the terminal. The other branched hole portion is closed.

4 Claims, 9 Drawing Sheets

(56)         References Cited

U.S. PATENT DOCUMENTS

| | | | | |
|---|---|---|---|---|
| 2007/0269060 A1 * | 11/2007 | Chou | ........................ | H04R 1/46 |
| | | | | 381/174 |
| 2015/0297170 A1 * | 10/2015 | Copt | ........................ | A61B 7/04 |
| | | | | 181/126 |
| 2018/0177482 A1 * | 6/2018 | Hashino | ............... | A61B 5/7285 |

FOREIGN PATENT DOCUMENTS

| | | | |
|---|---|---|---|
| CN | 107184231 A | | 9/2017 |
| JP | 2000-60845 A | | 2/2000 |
| JP | 2018-102849 A | | 7/2018 |
| JP | 2020-39706 A | | 3/2020 |

OTHER PUBLICATIONS

International Search Report for International Application No. PCT/JP2021/008091, dated May 11, 2921.

German Office Action for German Application No. 11 2021 000 563.4, dated Dec. 14, 2023, with English translation.

Written Opinion of the International Searching Authority for International Application No. PCT/JP2021/008091, dated May 11, 2021, with English Translation.

Chinese Office Action and Search Report for Chinese Application No. 202180017525.4, dated Nov. 21, 2024, with an English translation.

* cited by examiner

WHEEZE DETECTION DEVICE

CROSS-REFERENCE TO RELATED APPLICATIONS

This application is the U.S. national stage application filed pursuant to 35 U.S.C. 365(c) and 120 as a continuation of International Patent Application No. PCT/JP2021/008091, filed Mar. 3, 2021, which application claims priority to Japanese Patent Application No. 2020-057186, filed Mar. 27, 2020, which applications are incorporated herein by reference in their entireties.

TECHNICAL FIELD

The present invention relates to a wheeze detection device.

BACKGROUND ART

Patent Document 1 discloses a compact biological sound measurement apparatus that allows increasing an internal pressure of a space accommodating a sound detector to improve measurement sensitivity and allows maintaining the high internal pressure state over a long period of time. The biological sound measurement apparatus processes information of a biological sound detected by the sound detector for determination of whether wheezing is present, and notifies a user of the determination result by, for example, a sound or display.

CITATION LIST—PATENT LITERATURE

Patent Document 1: JP 2018-102849 A

SUMMARY OF INVENTION

Technical Problem

In order to analyze the biological sound and improve the determination accuracy when whether wheezing is present is determined, it is important to enhance sealability of the space accommodating the sound detector and improve the measurement sensitivity of the biological sound. On the other hand, it is also important to prevent superposition of a noise incorrectly detected as wheezing with a detection sound.

As a sound measurement element to measure a biological sound, an element having a method in which a measurement output changes according to a vibration state of a semiconductor element (for example, a Micro Electro Mechanical Systems (MEMS) microphone) has been known. When a degree of sealing of the space disposing the element is high, due to sudden internal pressure fluctuations of the space, such an element possibly generates a noise by vibration of the semiconductor element. That is, the sound measurement element itself possibly becomes a noise source and affects detection accuracy of wheezing.

An object of the present invention is to provide a wheeze detection device that allows suppressing a noise and improving detection accuracy of wheezing.

Solution to Problem

A wheeze detection device according to one aspect of the present invention will be described below. Note that, in the following parentheses, for example, corresponding components in embodiments described below are indicated but are not limited thereto.

(1); A wheeze detection device (a wheeze detection device 1) for detecting wheezing based on a sound measured from a living body while the wheeze detection device is in contact with a body surface of the living body. The wheeze detection device includes a sound measurement element (a first microphone M1), a space-forming member (a first housing 30, an O-ring 34, a flexible circuit board 35, and a second housing 33), and a cover member (a housing cover 36). The space-forming member forms an accommodation space (an accommodation space SP1) accommodating the sound measurement element. The cover member forms a pressure receiving unit (a pressure receiving unit 3a) that closes the accommodation space and receives a pressure from the body surface. The sound measurement element is an element (a MEMS microphone) having a method in which a measurement output changes according to a vibration state of a semiconductor element. The space-forming member has a hole portion (a hole portion 40) connected to an atmosphere. The accommodation space is connected to the atmosphere via the hole portion. The hole portion includes a branch portion (branch portions BR1 to BR3) between an inlet (a groove 41) on a side of the accommodation space and an outlet (a terminal 49) on a side of the atmosphere and two branched hole portions branched at the branch portion from a side of the inlet. One branched hole portion among the two branched hole portions is connected to the outlet. The other branched hole portion among the two branched hole portions is closed.

According to (1), presence of the hole portion can prevent the accommodation space from becoming a fully sealed state. For this reason, for example, it is possible to suppress sudden internal pressure fluctuations in the accommodation space that possibly occurs when, for example, a pressing position of the pressure receiving unit against the body surface changes. Therefore, measurement of a noise due to the internal pressure fluctuations by the sound measurement element can be prevented, and detection accuracy of wheezing can be enhanced. Additionally, since the hole portion has the branch portion, sealability of the accommodation space can be appropriately enhanced. Also, it is possible to enhance a sound insulation effect of a sound from the atmosphere side. Thus, the detection accuracy of wheezing can be improved.

(2); In the wheeze detection device according to (1), the hole portion further includes at least one branch portion in the one branched hole portion among the two branched hole portions.

According to (2), since the hole portion has the plurality of branch portions, sealability of the accommodation space and the sound insulation effect of the sound from the atmosphere side can be further enhanced. Thus, the detection accuracy of wheezing can be further improved.

(3); In the wheeze detection device according to (1) or (2), the space-forming member includes a tubular member (a first housing 30) and a placement member (a second housing 33). The tubular member has one end surface in an axial direction covered with the cover member. The placement member is fixed to another end surface in the axial direction of the tubular member in a way of closing an inner circumferential portion of the tubular member. The placement member is to place the sound measurement element. The hole portion is configured by a groove (the groove 41 to a groove 48) formed in the placement member.

According to (3), the hole portion can be easily formed.

Advantageous Effects of Invention

According to the present invention, the detection accuracy of wheezing can be improved.

DESCRIPTION OF EMBODIMENTS

Figure 1:
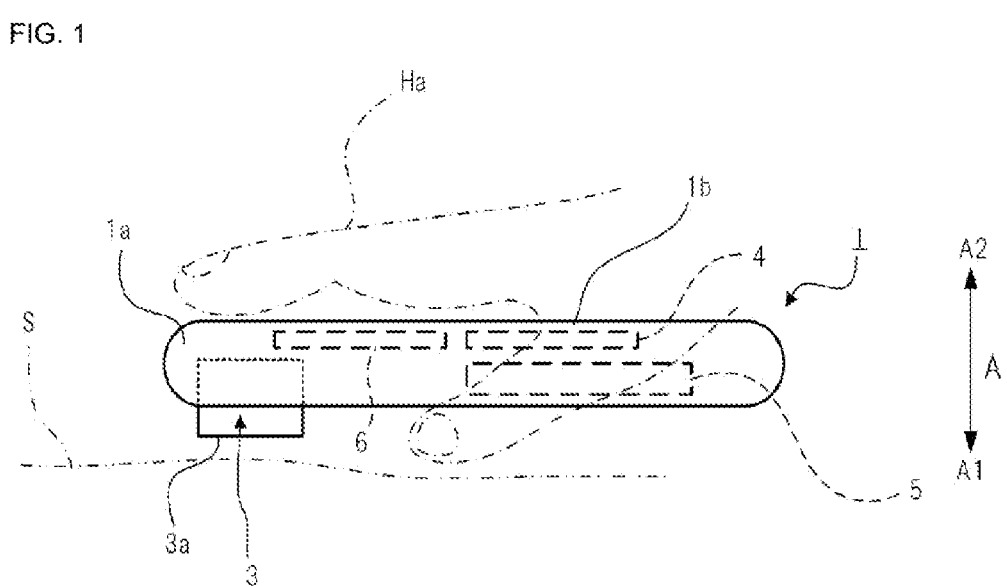
FIG. 1 is a side view illustrating a schematic configuration example of a wheeze detection device 1 as an embodiment of the present invention.

Overview of Wheeze Detection Device of Embodiment

First, an overview of a wheeze detection device according to an embodiment of the present invention will be described. The wheeze detection device according to the embodiment measures a sound (pulmonary sound) from a living body of a person and when wheezing is determined to be included in the measured sound, the wheeze detection device notifies the determination. In this way, it is possible to support the determination of the necessity of medication for the person to be measured, the determination of whether or not to take the person to the hospital, and the like.

The pulmonary sound occurs together with respiratory motion in a lung and a thorax and is all sounds except for a sound whose source is a cardiovascular system regardless of normal or abnormal. The pulmonary sound is classified into respiratory sounds, which are physiological sounds originating from a flow of air in an airway induced by breathing, and adventitious sounds, which are abnormal sounds caused by a sickness, such as wheezing and a pleural friction rub.

The wheeze detection device of the embodiment includes a measurement unit including an accommodation space that accommodates a sound measurement element.

The accommodation space is approximately sealed by a body surface and internal pressure fluctuations of the accommodation space in the state is detected by the sound measurement element, thus measuring the pulmonary sound of the living body. The sound measurement element is an element having a method in which a measurement output changes according to a vibration state of a semiconductor element.

The wheeze detection device according to the embodiment is configured to connect the accommodation space to an atmosphere to suppress sudden fluctuations in the internal pressure of the accommodation space when, for example, a contact position of the measurement unit with respect to the body surface changes. This configuration suppresses the sudden internal pressure fluctuations in the accommodation space, and thus the sound measurement element can be prevented from becoming a noise generating source.

When the sound measurement element emits a noise, this noise is possibly mistakenly recognized as wheezing. It has been found that such a noise remarkably occurs when a degree of sealing of the accommodation space for sound measurement element is high and measurement sensitivity of the sound measurement element is high. Enhancing the measurement sensitivity of the sound measurement element is important for measurement of a pulmonary sound with high accuracy. To enhance the measurement sensitivity of the sound measurement element, the use of an element (for example, a MEMS microphone) having a method in which a measurement output changes according to a vibration state of a fine semiconductor element is desirable.

The wheeze detection device according to the embodiment uses the sound measurement element having high measurement sensitivity to enhance the measurement accuracy of a pulmonary sound and connects the accommodation space to the atmosphere such that the sealing state of the accommodation space for sound measurement element is not fully sealed. As a result, even in a case where a situation in which the internal pressure of the accommodation space possibly suddenly increases (for example, a situation in which, after the measurement unit is brought into contact with the body surface to start measurement, the measurement unit is slightly separated from the body surface to move the position and is brought into contact with the body surface again to continue the measurement) occurs, the pressure inside the accommodation space can be released to the atmosphere. This allows suppressing a noise by the sound measurement element and allows enhancing the detection accuracy of wheezing. Details of the embodiment will be described below.

Embodiment

FIG. 1 is a side view illustrating a schematic configuration example of a wheeze detection device 1 as an embodiment of the wheeze detection device of the present invention. As illustrated in FIG. 1, the wheeze detection device 1 includes a rod-shaped gripping portion 1b, which is configured by a case made of, for example, resin or metal and a head portion 1a provided on one end side of the gripping portion 1b.

The gripping portion 1b is internally provided with an integrated control unit 4 that integrally controls the entire wheeze detection device 1, a battery 5 that supplies a necessary voltage for operation, and a display unit 6 that displays images via, for example, a liquid crystal display panel and an organic Electro Luminescence (EL) display panel.

The integrated control unit 4 includes, for example, a processor, a Random Access Memory (RAM), and a Read Only Memory (ROM) and, for example, controls each piece of hardware of the wheeze detection device 1 in accordance with a program.

The head portion 1*a* is provided with a measurement unit 3 that projects toward one side (downward in FIG. 1) in a direction roughly orthogonal to the longitudinal direction of the gripping portion 1*b*. The leading end of the measurement unit 3 is provided with a pressure receiving unit 3*a* that is brought into contact with a body surface S of a living body, i.e., a subject, and receives pressure from the body surface S.

The wheeze detection device 1 is used by the pressure receiving unit 3*a* of the measurement unit 3 being pressed by a user's hand Ha, for example, an index finger against the body surface S, with the index finger being placed on the back surface of the measurement unit 3 in the head portion 1*a*. Hereinafter, the pressing direction (the downward direction in FIG. 1) of the pressure receiving unit 3*a* to body surface S is described as a direction A1, a direction opposite to the direction A1 is described as a direction A2, and the direction A1 and the direction A2 are collectively described as a direction A.

Figure 2:
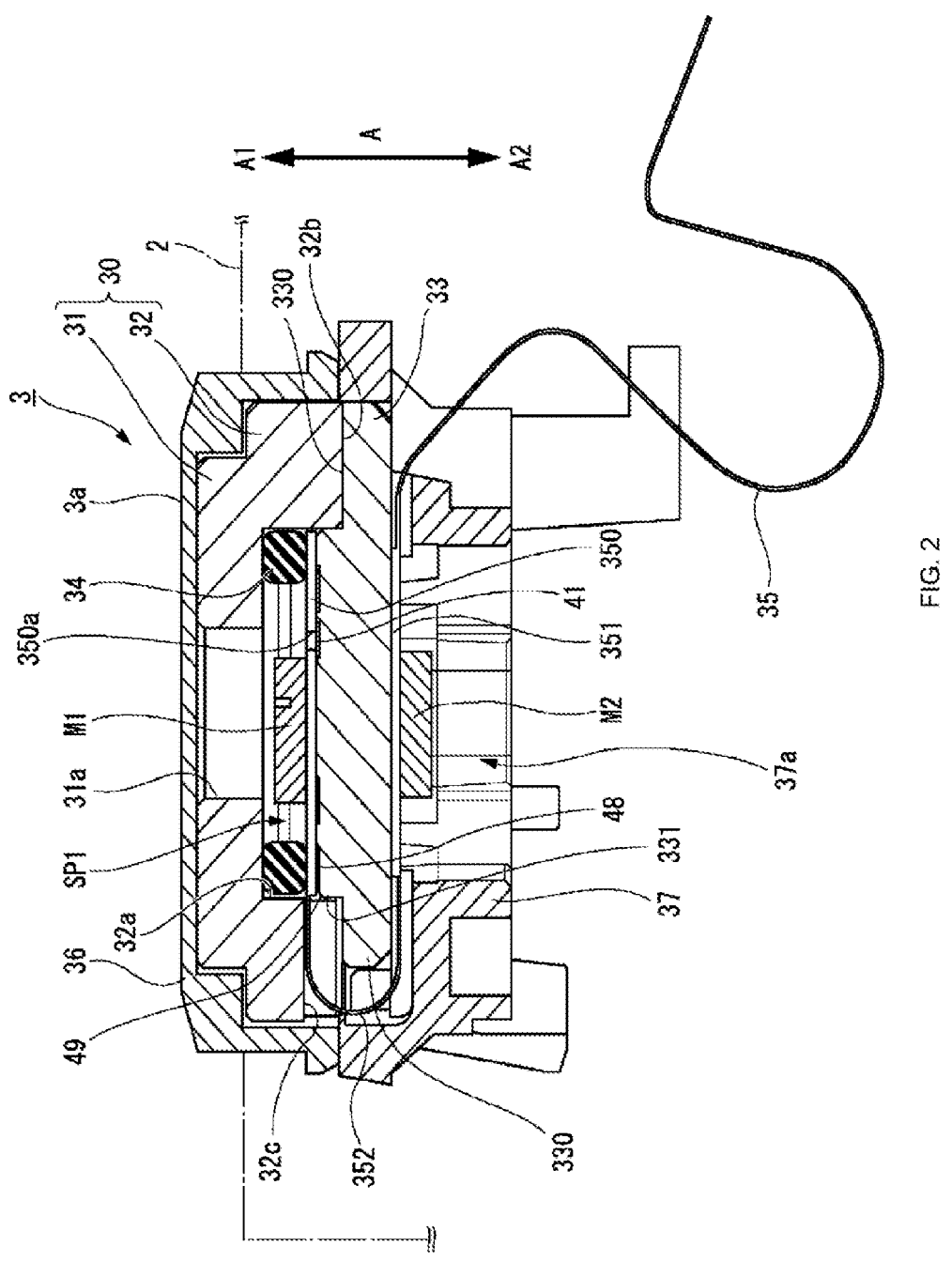
FIG. 2 is a schematic cross-sectional view of a measurement unit 3 of the wheeze detection device 1 illustrated in FIG. 1.
Figure 3:
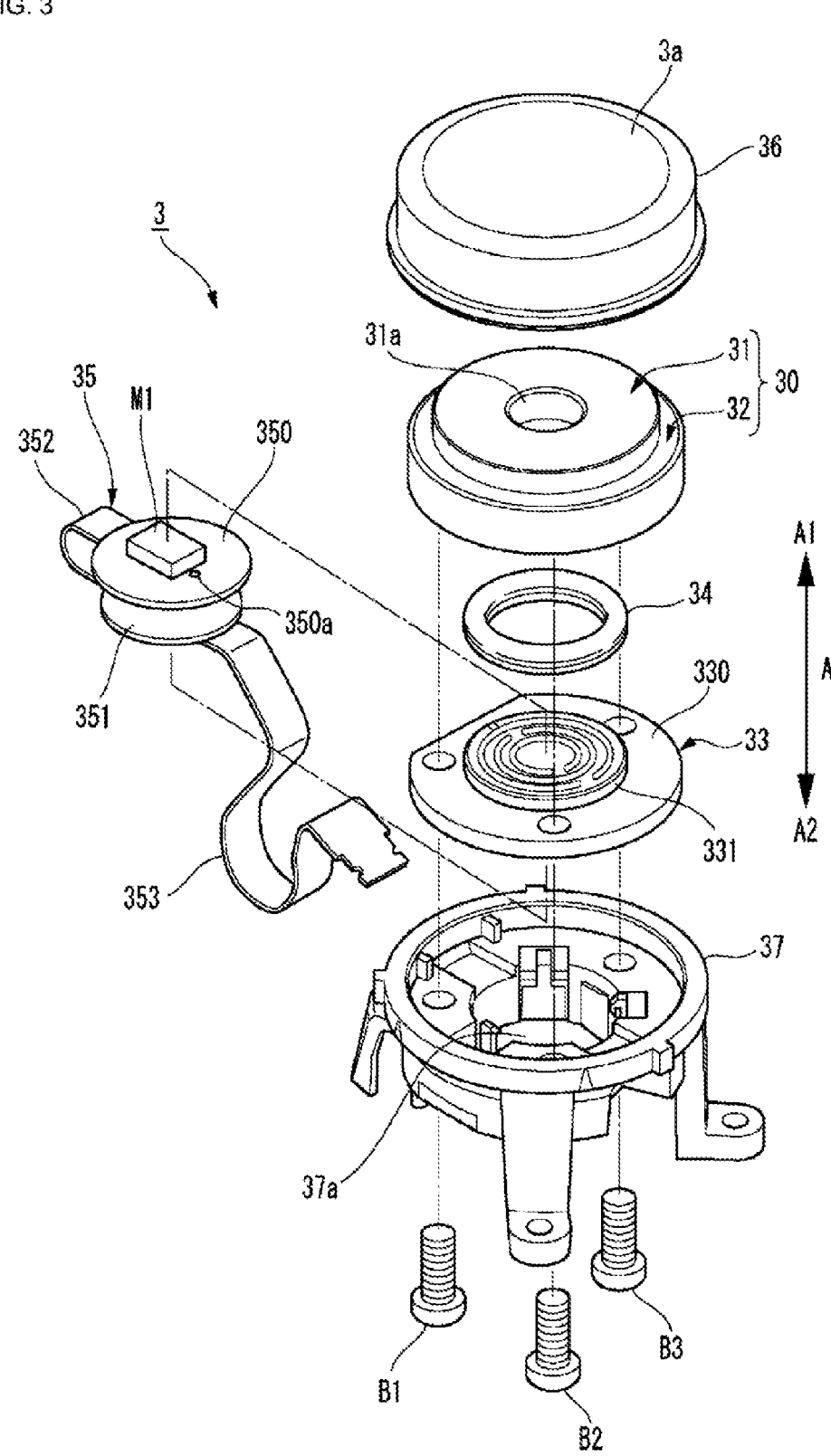
FIG. 3 is a schematic exploded view of the measurement unit 3 of the wheeze detection device 1 illustrated in FIG. 1 as viewed obliquely from a direction A1 side.
Figure 4:
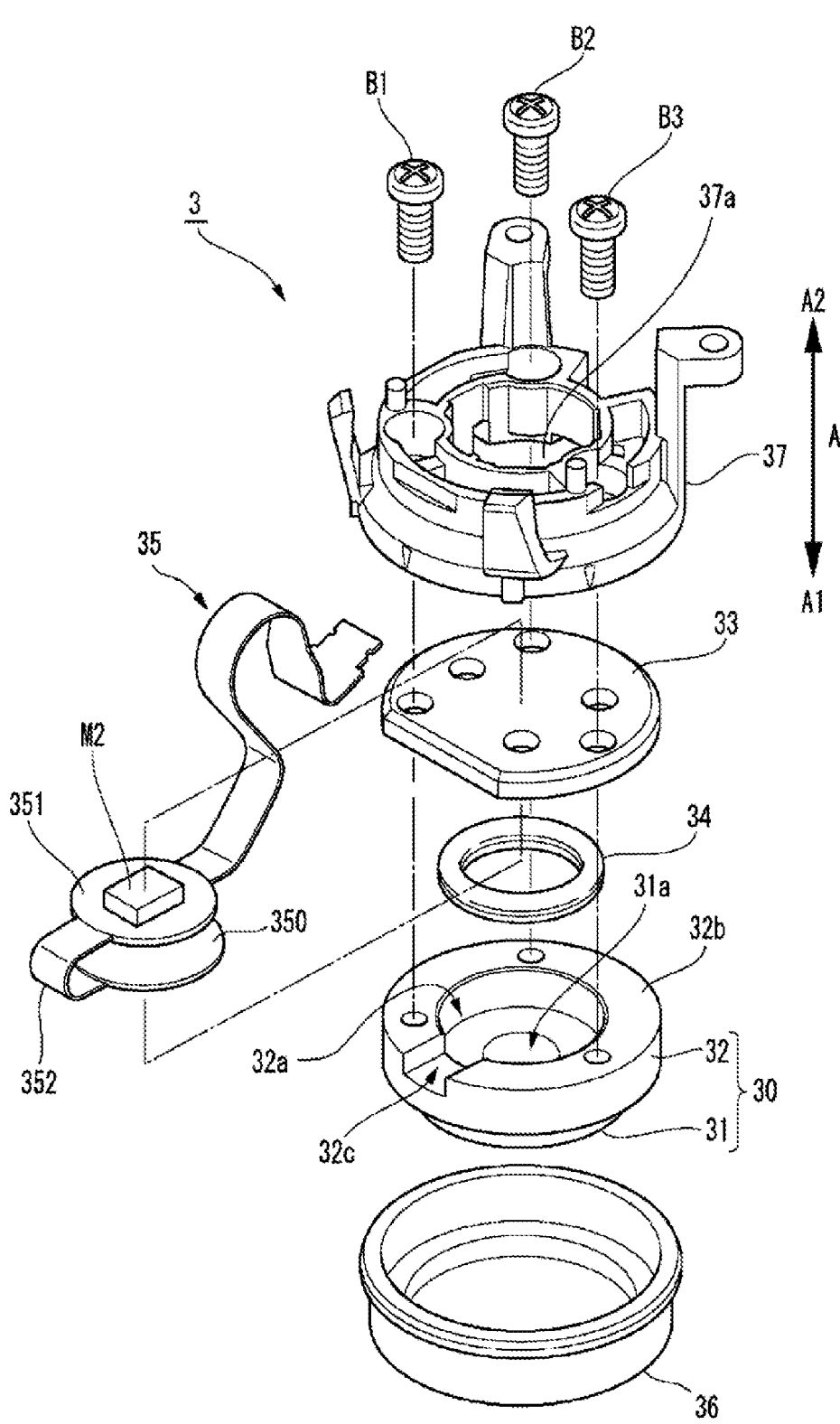
FIG. 4 is a schematic exploded view of the measurement unit 3 of the wheeze detection device 1 illustrated in FIG. 1 as viewed obliquely from a direction A2 side.
Figure 5:
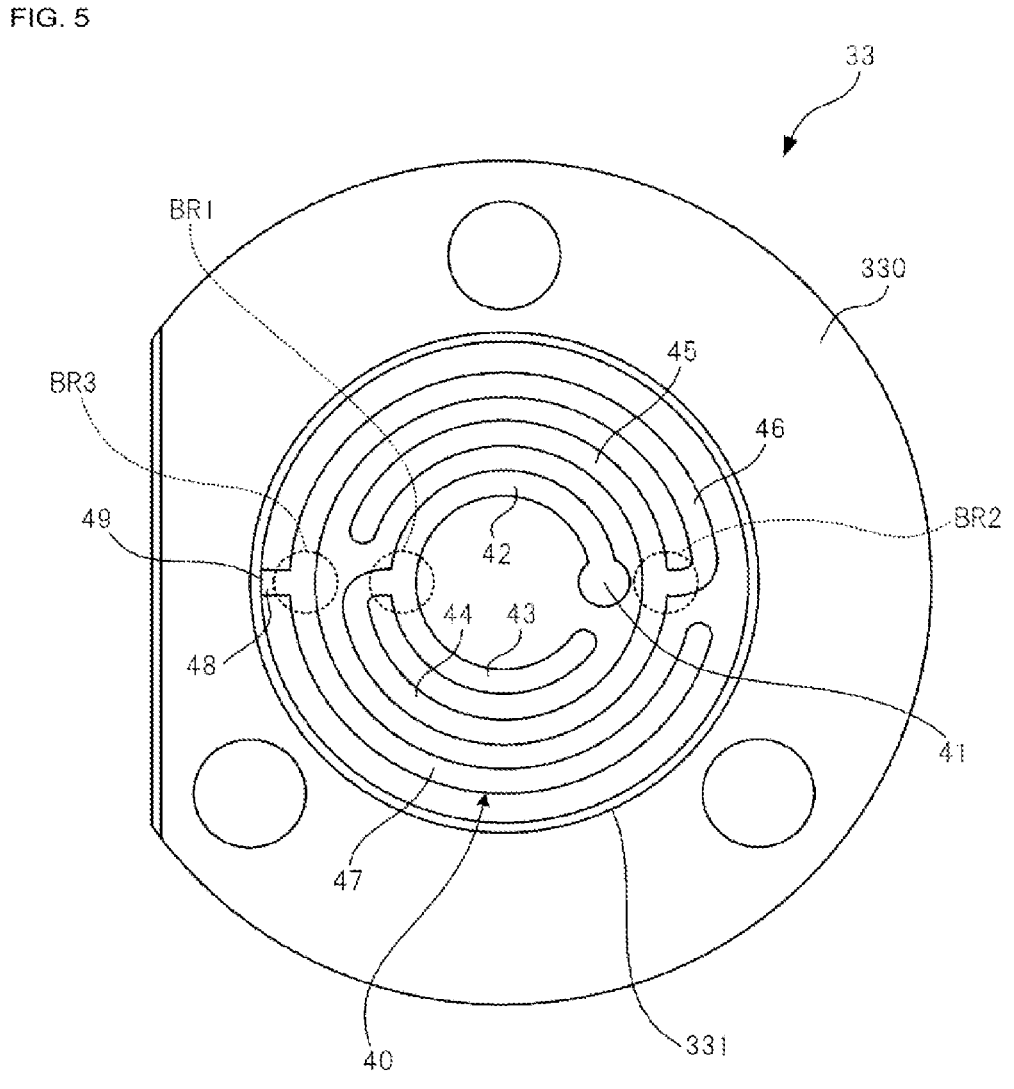
FIG. 5 is a schematic plan view of a second housing 33 in the measurement unit 3 illustrated in FIG. 2 to FIG. 4 as viewed in the direction A2.
Figure 6:
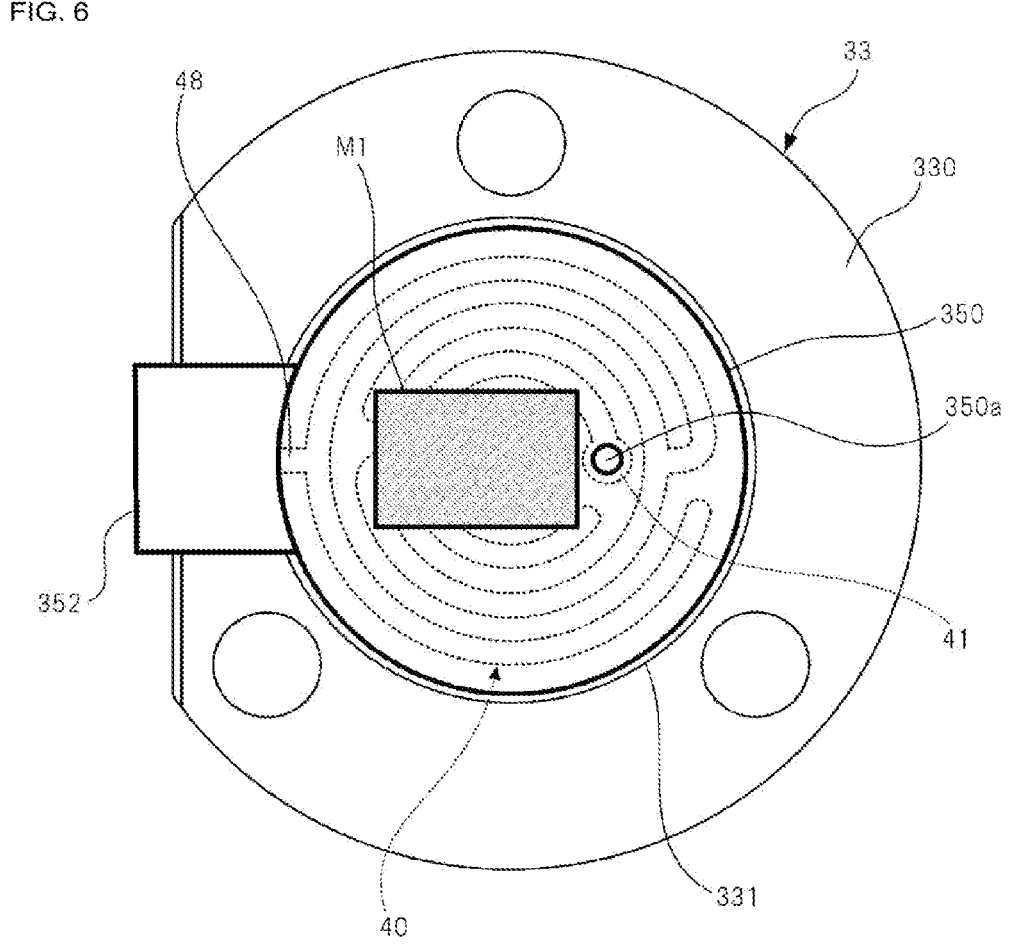
FIG. 6 is a schematic plan view of the second housing 33 and a flexible circuit board 35 in the measurement unit 3 illustrated in FIG. 2 to FIG. 4 as viewed in the direction A2.

FIG. 2 is a schematic cross-sectional view of the measurement unit 3 of the wheeze detection device 1 illustrated in FIG. 1. FIG. 3 is a schematic exploded view of the measurement unit 3 of the wheeze detection device 1 illustrated in FIG. 1 as viewed obliquely from the direction A1 side. FIG. 4 is a schematic exploded view of the measurement unit 3 of the wheeze detection device 1 illustrated in FIG. 1 as viewed obliquely from the direction A2 side. FIG. 5 is a schematic plan view of a second housing 33 in the measurement unit 3 illustrated in FIG. 2 to FIG. 4 as viewed in the direction A2. FIG. 6 is a schematic plan view of the second housing 33 and a flexible circuit board 35 in the measurement unit 3 illustrated in FIG. 2 to FIG. 4 as viewed in the direction A2.

The measurement unit 3 includes a housing cover 36, a first housing 30, an O-ring 34, the second housing 33, the flexible circuit board 35 on which a first microphone M1 and a second microphone M2 are mounted, and a case 37 that supports the first housing 30, the O-ring 34, the second housing 33, and the flexible circuit board 35.

As illustrated in FIG. 2, the measurement unit 3 is engaged with an opening portion formed in a case 2 forming the head portion 1*a*, with a portion of the housing cover 36 exposed. The case 37 of the measurement unit 3 is supported by this case 2. A leading end portion of the portion of the housing cover 36 exposed from the case 2 is shaped as a flat surface or a curved surface, with this flat surface or curved surface forming the pressure receiving unit 3*a*.

The first housing 30 is constituted by a tubular member. The first housing 30 is made of a material having higher acoustic impedance than that of air and high rigidity, such as resin or metal. The first housing 30 is preferably made of a material that reflects a sound in a measurement frequency band of the first microphone M1, making it difficult for a sound from the outside to transmit to an accommodation space SP1 described later when the pressure receiving unit 3*a* is in contact with the body surface S.

In the example illustrated in FIG. 2 to FIG. 4, the first housing 30 is a substantially cylindrical member having a convex shape convex toward the direction A1 provided with a small diameter portion 31 and a large diameter portion 32 having an outer diameter greater than that of the small diameter portion 31. As illustrated in FIG. 2 to FIG. 4, a hollow portion is formed inside the first housing 30. The hollow portion is configured by a first recessed portion 32*a* formed in an end surface 32*b* on the direction A2 side of the large diameter portion 32 to form a substantially columnar space and an opening 31*a* formed at the center of the bottom surface of the first recessed portion 32*a* and having a diameter smaller than that of the first recessed portion 32*a*. Additionally, in a portion of the end surface 32*b* of the first housing 30, a second recessed portion 32*c* that reaches the side surface of the large diameter portion 32 from the first recessed portion 32*a* is formed.

The housing cover 36 is a tubular member with a closed bottom, and the shape of the hollow portion of the housing cover 36 is substantially the same as the shape of the outer circumferential surface (excluding the end surface 32*b*) of the first housing 30. The first housing 30 is inserted into and fitted to the hollow portion of the housing cover 36, and the outer circumferential surface of the first housing 30 (in particular, the end surface on the direction A1 side) and the housing cover 36 are in close contact. In this way, the first housing 30 has a configuration in which one end face (the end face on the direction A1 side) in an axial direction of the first housing 30 is covered with the housing cover 36. The housing cover 36 is made of a material with an acoustic impedance that is close to that of a human body, air, or water and having flexibility and good biocompatibility. Examples of the material of the housing cover 36 include silicone and an elastomer.

As illustrated in FIG. 3 to FIG. 5, the second housing 33 has a shape in which a portion of a circular plate is cut away, and a substantially columnar protrusion portion 331 is formed in a surface 330 on the direction A1 side. The diameter of the protrusion portion 331 is slightly smaller than the diameter of the first recessed portion 32*a* of the first housing 30. The second housing 33 is fixedly secured to the first housing 30 in the form of closing the first recessed portion 32*a* of the first housing 30 with screws 131 to B3 passing through respective three screw holes formed in portions excluding the protrusion portion 331. More specifically, the surface 330 of the second housing 33 and the end surface 32*b* of the first housing 30 are butted, and the first recessed portion 32*a* of the first housing 30 is blocked by the second housing 33.

The O-ring 34 has the outer diameter smaller than the diameter of the first recessed portion 32*a* of the first housing 30 and is accommodated in the first recessed portion 32*a* of the first housing 30. The outer diameter of the O-ring 34 is substantially the same as the outer diameter of the protrusion portion 331 of the second housing 33.

The flexible circuit board 35 is a circuit board having flexibility and includes a substantially circular plate-shaped flat plate portion 350 on which the first microphone M1 is mounted, a substantially circular plate-shaped flat plate portion 351 on which the second microphone M2 is mounted, a coupling portion 352 that couples the flat plate portion 350 and the flat plate portion 351, and a long portion 353 extending from the side opposite to the coupling portion 352 side of the flat plate portion 351. The long portion 353 is connected to a substrate on which, for example, the integrated control unit 4 illustrated in FIG. 1 is mounted. Sound information measured by each of the first microphone M1 and the second microphone M2 is transmitted to the integrated control unit 4 via the flexible circuit board 35.

The first microphone M1 is a sound measurement element to measure the pulmonary sound and is configured by, for example, a Micro Electro Mechanical Systems (MEMS) microphone or a capacitance microphone that detects sounds in a band (for example, a frequency range ranging from 1 Hz to 10 kHz) wider than the frequency range (typically, a range from 10 Hz to 1.5 kHz) of pulmonary sounds, for example.

As illustrated in FIG. 6, the flat plate portion 350 on which the first microphone M1 is mounted has substantially the same size as the protrusion portion 331 of the second housing 33 as viewed in the direction A. As illustrated in FIG. 2, the flat plate portion 350 is disposed between the O-ring 34 and the protrusion portion 331 of the second housing 33. A through hole 350a is formed in the flat plate portion 350. The first microphone M1 mounted on the flat plate portion 350 and the through hole 350a of the flat plate portion 350 are disposed inside the O-ring 34.

A thickness A in the A direction of the O-ring 34 is greater than a distance between the flat plate portion 350 and the bottom surface of the first recessed portion 32a of the first housing 30 in the assembled state illustrated in FIG. 2. Therefore, in the assembled state of FIG. 2 in which the first housing 30 and the second housing 33 are fixedly secured with the screws B1 to B3, the flat plate portion 350 is in close contact with the surface of the protrusion portion 331.

The second microphone M2 is a different (from the first microphone M1) sound measurement element for measuring a sound around the measurement unit 3 (such as an environmental sound of, for example, a voice of a person or a rubbing noise between the wheeze detection device 1 and a living body or a garment), and, for example, configured by a MEMS microphone or a capacitive microphone that measures a sound in a band wider than the frequency range of the pulmonary sound (for example, a frequency range from 10 Hz to 10 kHz).

As illustrated in FIG. 2, the flat plate portion 351 on which the second microphone M2 is mounted is fixedly secured to the surface (the surface on the direction A2 side) on the side opposite to the protrusion portion 331 side of the second housing 33 by, for example, an adhesive. The coupling portion 352 of the flexible circuit board 35 passes through the second recessed portion 32c of the first housing 30 to reach the inside of the case 37.

The case 37 has a tubular shape having a hollow portion 37a. The first housing 30 and the second housing 33 are fixed to the inner circumferential portion of the case 37 with the screws B1 to B3. As illustrated in FIG. 2, the second microphone M2 mounted on the flat plate portion 351 of the flexible circuit board 35 is exposed to the hollow portion 37a of the case 37. This hollow portion 37a is open to the atmosphere.

As illustrated in FIG. 5 and FIG. 6, a hole portion 40 formed by grooves having a substantially spiral shape (or a substantially concentric circle shape) is provided on the surface of the protrusion portion 331 of the second housing 33. The hole portion 40 is configured by grooves 41 to 48.

The groove 41 is a substantially circular groove having a size greater than that of the through hole 350a formed at a position facing the through hole 350a of the flexible circuit board 35. The groove 42 is a substantially arc-shaped groove extending counterclockwise from the groove 41.

The groove 43 is a substantially arc-shaped groove extending counterclockwise from the terminal portion of the groove 42 toward the groove 41. The terminal of the groove 43 is closed without joining to another groove. The groove 44 is a substantially arc-shaped groove extending counterclockwise outside the groove 43 (radially outward of the protrusion portion 331) from the terminal portion of the groove 42 along the groove 43.

The groove 45 is a substantially arc-shaped groove extending counterclockwise outside the groove 42 from the terminal portion of the groove 44 along the groove 42. The terminal of the groove 45 is closed without joining to another groove. The groove 46 is a substantially arc-shaped groove extending counterclockwise outside the groove 45 from the terminal portion of the groove 44 along the groove 45.

The groove 47 is a substantially arc-shaped groove extending counterclockwise outside the groove 44 from the terminal portion of the groove 46 along the groove 44. The terminal of the groove 47 is closed without joining to another groove. The groove 48 is a linear groove extending to the surface 330 side (radially outward) of the second housing 33 from the terminal portion of the groove 46. The terminal of the groove 48 is exposed to the second recessed portion 32c of the first housing 30 in the assembled state illustrated in FIG. 2.

In this way, the hole portion 40 formed in the surface of the protrusion portion 331 of the second housing 33 has three branch portions (a branch portion BR1 formed at the terminal of the groove 42, a branch portion BR2 formed at the terminal of the groove 44, and a branch portion BR3 formed at the terminal of the groove 46) where the grooves are branched into two between the groove 41 and the terminal 49 of the groove 48.

In the assembled state illustrated in FIG. 2, as illustrated in FIG. 6, the through hole 350a of the flexible circuit board 35 overlaps with the groove 41. Additionally, the hole portion 40 is covered with the flat plate portion 350 of the flexible circuit board 35 and sealed by the flat plate portion 350 except for the terminal of the groove 48 and a portion of the groove 41.

As illustrated in FIG. 2, the first microphone M1 is accommodated in the accommodation space SP1 surrounded by the O-ring 34, the flat plate portion 350, the inner circumferential surface of the first housing 30, and the housing cover 36. The O-ring 34, the flat plate portion 350, the first housing 30, the second housing 33, and the housing cover 36 constitute a space-forming member that forms the accommodation space SP1.

In a case where there is no through hole 350a in the flat plate portion 350, the accommodation space SP1 can be a space sealed with high airtightness (for example, a space having a pressure higher than an atmosphere pressure). In the present embodiment, the accommodation space SP1 is connected to the atmosphere via the through hole 350a and the hole portion 40 connected to the through hole 350a. In the hole portion 40, the groove 41 constitutes an inlet on the accommodation space SP1 side, and the terminal 49 of the groove 48 constitutes an outlet on the atmosphere side.

During use of the wheeze detection device 1 configured as described above, the pressure receiving unit 3a of the housing cover 36 contacts the body surface S. Then, when the pressure receiving unit 3a vibrates due to the pulmonary sounds transmitted from the living body to the body surface S, the internal pressure of the accommodation space SP1 fluctuates due to this vibration, and by the internal pressure fluctuations, an electrical signal corresponding to the pulmonary sound is detected by the first microphone M1. Also, the second microphone M2 measures the surrounding sound while the wheeze detection device 1 is used.

The integrated control unit 4 performs a process for determining whether wheezing is present based on the sound measured by the first microphone M1 and the sound measured by the second microphone M2. For example, the integrated control unit 4 removes an ambient noise other than a pulmonary sound that mixes with a first sound measured by the first microphone M1 based on a second sound measured by the second microphone M2. The integrated control unit 4 determines the presence or absence of wheezing based on the first sound after the ambient noise is removed. Note that the second microphone M2 is not essential, and the presence or absence of wheezing may be determined based on the sound measured by the first microphone M1. Various methods can be employed as the method for determining the presence or absence of wheezing.

Effects of Wheeze Detection Device

During the measurement of the pulmonary sound by the first microphone M1, for example, in a case where the way of pressing the pressure receiving unit 3a against the body surface is changed or the pressing position of the pressure receiving unit 3a is changed, when the degree of sealing of the accommodation space SP1 is excessively high, the internal pressure of the accommodation space SP1 possibly substantially fluctuates. According to the wheeze detection device 1, even when the internal pressure of the accommodation space SP1 changes to increase, for example, the air in the accommodation space SP1 is released to the atmosphere via the through hole 350a and the hole portion 40, and thus large fluctuations in the internal pressure of the accommodation space SP1 can be suppressed. As a result, a noise caused by the first microphone M1 itself can be suppressed when the MEMS microphone is used as the first microphone M1 can be suppressed (hereinafter described as a noise suppression effect) and the detection accuracy of wheezing can be enhanced.

Additionally, the hole portion 40 with the configuration illustrated in FIG. 5 has a configuration of including the grooves with the closed terminals, the groove connected to the terminal 49, and the branch portions (the branch portions BR1 to BR3) where the grooves are branched into two between the inlet (the groove 41) on the accommodation space SP1 side and the outlet (the terminal 49) on the atmosphere side.

According to this configuration, when an ambient sound enters from the terminal 49, which is connected to the atmosphere, energy of the ambient sound can be attenuated at the closed groove branched at each of the branch portions. As a result, a sound pressure of the ambient sound reaching the accommodation space SP1 can be sufficiently reduced. That is, a sound insulation effect of a sound from the atmosphere side can be increased. In this way, it is possible to improve the detection accuracy of wheezing by enhancing the sound insulation effect. Conversely, it can be said that this structure does not cause the pressure of the accommodation space SP1 to excessively escape to the atmosphere. That is, the wheeze detection device 1 can prevent the sealing state of the accommodation space SP1 from becoming excessively low. As a result, the pulmonary sound can be measured with high sensitivity (hereinafter described as a measurement accuracy improvement effect), and wheezing detection accuracy can be enhanced.

Note that, as long as the hole portion 40 is configured to include at least one branch portion, the sound insulation effect and the measurement accuracy improvement effect can be obtained. Note that providing the plurality of, preferably three as in FIG. 5, branch portions allows obtaining the effects further strongly.

As a result of verification, in the configuration of the hole portion 40 illustrated in FIG. 5, when a cross-sectional area of the through hole 350a of the flexible circuit board 35 is set to be 0.1964 mm$^2$ and a cross-sectional area of each of the grooves 42 to the groove 48 is set to be 0.045 mm$^2$ or less, configuring the total length of the groove 42, the groove 44, the groove 46, and the groove 48 so as to be 20 mm or more or preferably 30 mm or more allows enhancing wheeze detection accuracy with an optimal balance between the noise suppression effect, the sound insulation effect, and the measurement accuracy improvement effect.

Modified Example of Hole Portion

In the above-described embodiment, the hole portion 40 has the substantially spiral shape (substantially concentric circle shape), but in a first modified example and a second modified example described below, the hole portion 40 has a linear shape, which differs from the above-described embodiment.

Figure 7:
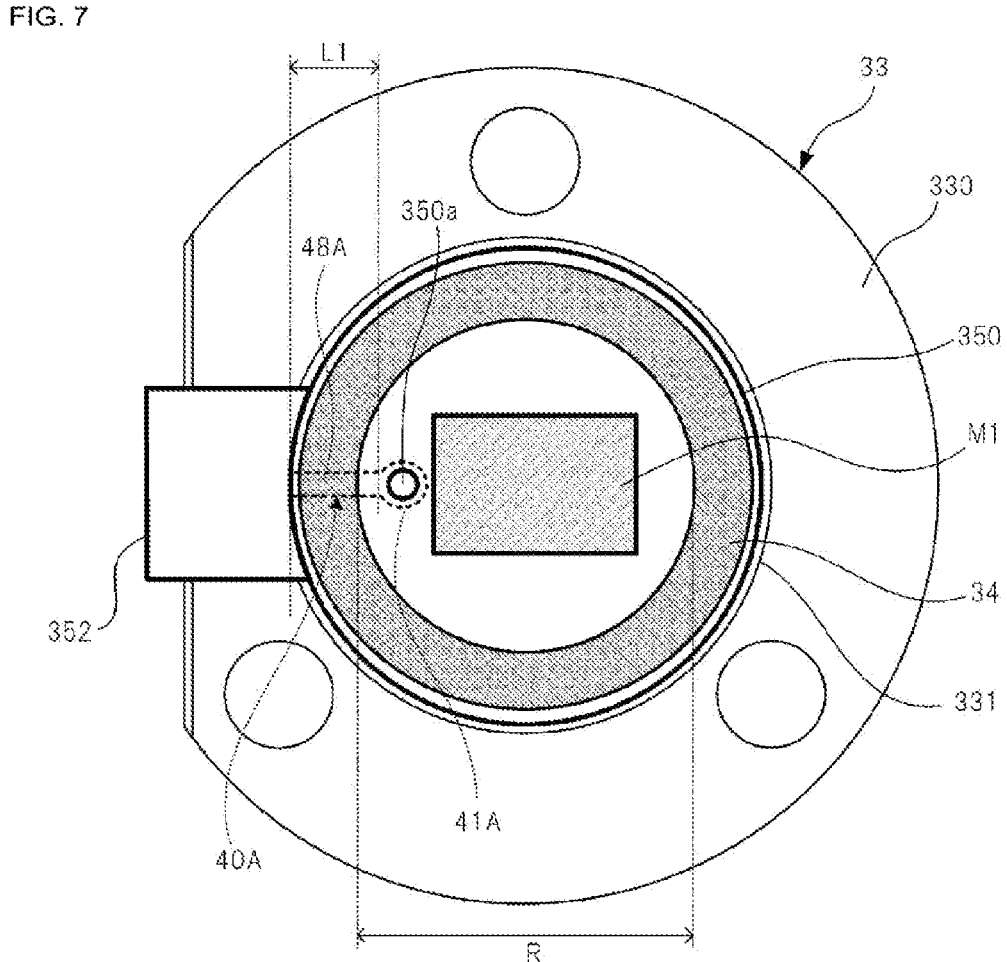
FIG. 7 is a schematic plan view for describing a hole portion according to a first modified example formed in the second housing 33.

FIG. 7 is a schematic plan view for describing the hole portion according to the first modified example formed in the second housing 33. FIG. 7 illustrates the second housing 33 and the flexible circuit board 35 and the O-ring 34 that overlap with the second housing 33. In the first modified example, the positional relationship between the first microphone M1 and the through hole 350a in the flat plate portion 350 of the flexible circuit board 35 is reversed from the embodiment described above.

In the first modified example illustrated in FIG. 7, a hole portion 40A is formed in the surface of the protrusion portion 331 of the second housing 33. The hole portion 40A includes a groove 41A having a substantially circular shape overlapping with the through hole 350a and having a diameter greater than that of the through hole 350a, and a rectangular groove 48A linearly extending outward in the radial direction of the protrusion portion 331 from the groove 41A. The terminal of the groove 48A is exposed to the second recessed portion 32c of the first housing 30, similar to the terminal 49 of the hole portion 40.

Figure 8:
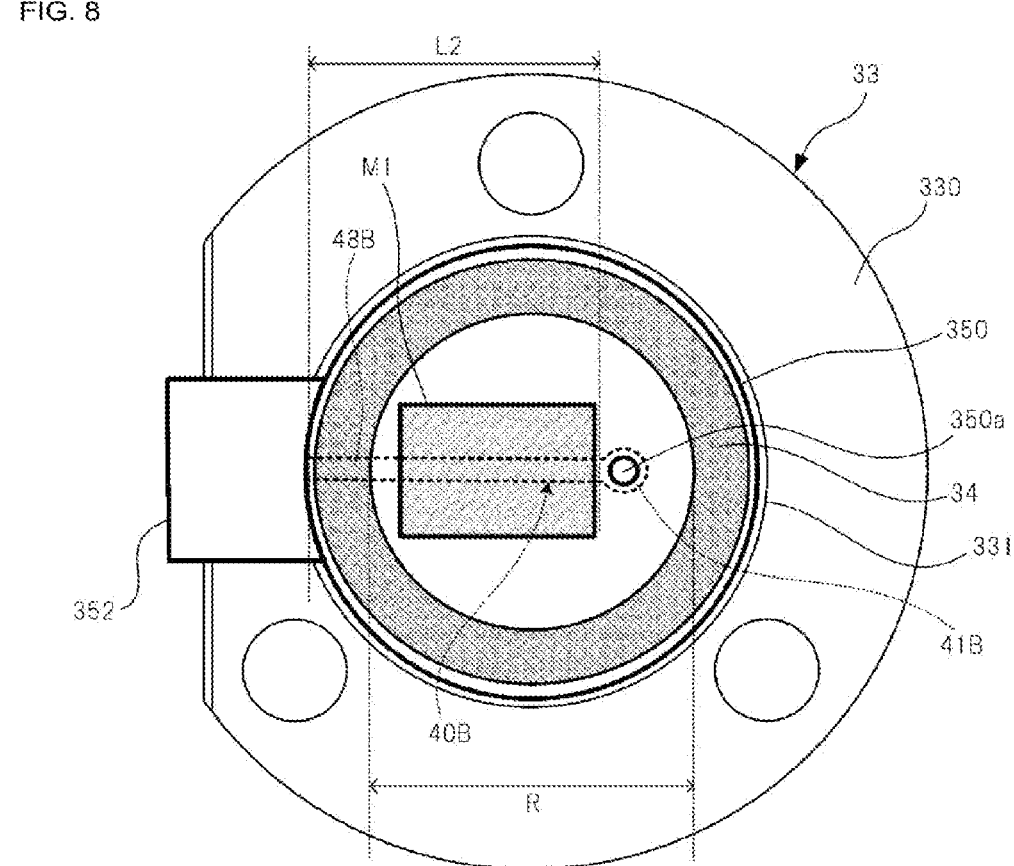
FIG. 8 is a schematic plan view for describing a hole portion according to a second modified example formed in the second housing 33.

FIG. 8 is a schematic plan view for describing a hole portion according to the second modified example formed in the second housing 33. FIG. 8 illustrates the second housing 33 and the flexible circuit board 35 and the O-ring 34 that overlap with the second housing 33.

In the second modified example illustrated in FIG. 8, a hole portion 40B is formed in the surface of the protrusion portion 331 of the second housing 33. The hole portion 408 includes a groove 41B having a substantially circular shape overlapping with the through hole 350a and having a diameter greater than that of the through hole 350a, and a rectangular groove 48B linearly extending from the groove 41B to the coupling portion 352 side. The terminal of the groove 48B is exposed to the second recessed portion 32c of the first housing 30, similar to the terminal 49 of the hole portion 40.

In the first modified example and the second modified example, the accommodation space SP1 is connected to the atmosphere by the through holes 350a and the linear hole portions 40A and 40B connected to the through holes 350a. According to the configuration, even when the internal pressure of the accommodation space SP1 changes to increase, for example, the air in the accommodation space SP1 is released to the atmosphere via the through hole 350a and the hole portion 40A or 40B, and thus large fluctuations in the internal pressure of the accommodation space SP1 can be suppressed. As a result, a noise caused by the first microphone M1 itself can be suppressed when the MEMS microphone is used as the first microphone M1 can be suppressed and the detection accuracy of wheezing can be enhanced.

Additionally, since the hole portions 40A and 40B have the linear shapes, compared with the hole portion 40 having the branch portions, the flow of air from the accommodation space SP1 to the atmosphere can be smoothed. In other words, a fluid resistance of the hole portion 40 can be reduced. In other words, according to the first modified example and the second modified example, the degree of sealing of the accommodation space SP1 can be lower than that of the configuration of the embodiment described above. Thus, the noise generated by the first microphone M1 itself can be strongly suppressed and wheezing detection accuracy can be further enhanced more than those in the above-described embodiment.

The hole portion 40B in FIG. 8 is configured to be longer than the hole portion 40A in FIG. 7. Thus, according to the configuration illustrated in FIG. 8, compared with the configuration illustrated in FIG. 7, the excessive decrease in the degree of sealing of the accommodation space SP1 can be prevented. Conversely, according to the configuration illustrated in FIG. 8, compared with the configuration illustrated in FIG. 7, the sound insulation effect from the atmosphere to the accommodation space SP1 can be enhanced.

On the other hand, the hole portion 40A is configured to be shorter than the hole portion 40B. Thus, according to the configuration illustrated in FIG. 7, compared with the configuration illustrated in FIG. 8, the degree of sealing of the accommodation space SP1 can be reduced.

Thus, with the use of the linear hole portion 40, adjusting the length allows adjusting the balance between the noise suppression effect, the sound insulation effect, and the measurement accuracy improvement effect. Note that the length of the hole portion 40A or 40B refers to the length of the portion except for the groove 41A or 41B at the inlet.

For example, a length L1 of the hole portion 40A (a length of the groove 48A) is less than the half of a width R (equivalent to the inner diameter of the O-ring 34) in a direction perpendicular to the direction A of the accommodation space SP1. By setting the length L1 to be less than the half of the width R, the sealability of the accommodation space SP1 can be sufficiently reduced, and the noise suppression effect of the first microphone M1 can be enhanced.

Also, a length L2 of the hole portion 40B (a length of the groove 48B) is equal to or greater than the half of the width R of the accommodation space SP1. Setting the length L2 to be the half or more of the width R slightly reduces the noise suppression effect. However, the balance between the noise suppression effect, the sound insulation effect, and the measurement accuracy improvement effect can be substantially equivalent, and wheezing detection accuracy can be enhanced.

As a result of further detailed verification, with the configuration of the hole portion 40A (or the hole portion 40B), when the cross-sectional area of the through hole 350a of the flexible circuit board 35 is set to be 0.1964 mm² and the cross-sectional area (the area of the cross-section perpendicular to the groove extending direction) of the groove 48A (or the groove 48B) is set to be 0.045 mm² (the width of the groove=0.5 mm and the depth of 0.09 mm) or less, setting the length of the groove 48A (or the groove 488) to be 3 mm or more and less than 7 mm allows increasing wheezing detection accuracy. Specifically, setting the length to be 3 mm or more and less than 7 mm slightly reduces the measurement accuracy of the pulmonary sound and sound insulation performance compared with the configuration having the length of 7 mm or more, but the noise suppression effect of the first microphone M1 can be enhanced. Therefore, it is possible to increase the wheezing detection accuracy by the balance between the measurement accuracy of a pulmonary sound, the sound insulation performance, and noise suppression performance.

Furthermore, setting the length to be 7 mm or more and 15 mm or less allows further enhancing of wheezing detection accuracy. Specifically, setting the length to be 7 mm or more and less than 15 mm slightly weakens the noise suppression effect of the first microphone M1 compared with the configuration in which the length is less than 7 mm. However, the measurement accuracy of a pulmonary sound and the sound insulation performance are improved. Therefore, wheezing detection accuracy can be further enhanced by the balance between the measurement accuracy of a pulmonary sound, the sound insulation performance, and the noise suppression performance. Note that the reason that the upper limit value of the cross-sectional area of the groove 48A (or the groove 48B) is set to be 0.045 mm² is that the cross-sectional area in excess of the value excessively decreases the sealing property of the accommodation space SP1 regardless of the length of the groove 48A (or the groove 48B) and a degree of decrease in wheezing detection accuracy due to the decrease in the sound insulation performance and the measurement accuracy of a pulmonary sound becomes excessively greater than a degree of increase in wheezing detection accuracy due to improvement in noise suppression effect.

Figure 9:
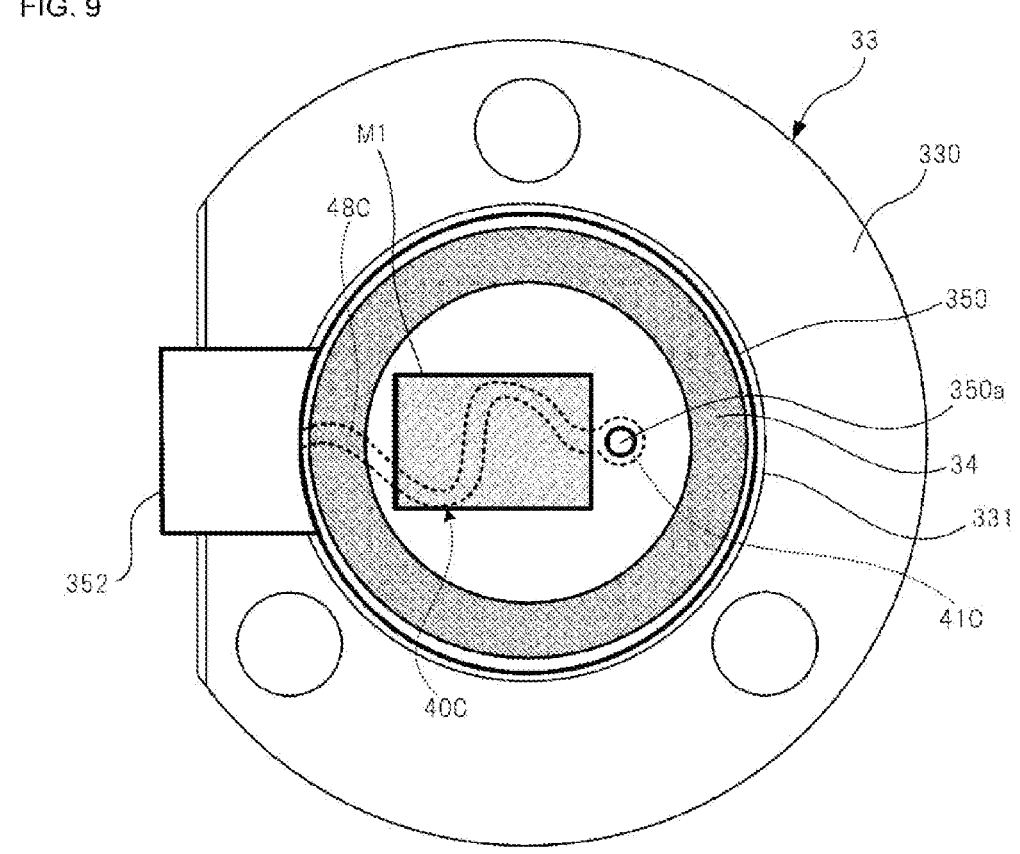
FIG. 9 is a schematic plan view for describing a hole portion according to a third modified example formed in the second housing 33.

FIG. 9 is a schematic plan view for describing a hole portion according to a third modified example formed in the second housing 33. FIG. 9 illustrates the second housing 33 and the flexible circuit board 35 and the O-ring 34 that overlap with the second housing 33.

In the third modified example illustrated in FIG. 9, a hole portion 40C is formed in the surface of the protrusion portion 331 of the second housing 33. The hole portion 40C includes a groove 41C having a substantially circular shape overlapping with the through hole 350a and having a diameter greater than that of the through hole 350a, and a groove 48C having a meandering curved line shape extending from the groove 41C toward the coupling portion 352 side. The terminal of the groove 48C is exposed to the second recessed portion 32c of the first housing 30, similar to the terminal 49 of the hole portion 40.

In this manner, the hole portion 40C has the shape including the curved lines, and thus, compared with the hole portions 40A and 40B, it is possible to obtain an effect of preventing flow of air from the accommodation space SP1 to the atmosphere. In other words, the fluid resistance in the hole portion 40C can be reduced. That is, according to the third modified example, even when the length of the groove 48C is the same as that of the groove 48A and the groove 48B, the degree of sealing of the accommodation space SP1 can be lower than those of the first modified example and the second modified example. Therefore, the noise of the first microphone M1 itself can be strongly suppressed, and wheezing detection accuracy can be further enhanced. Additionally, the sound insulation performance can be enhanced and the measurement accuracy of a pulmonary sound can be improved.

In the description described above, the respective hole portions 40, 40A, 40B, and 40C are the grooves. However, each of the hole portions 40, 40A, 40B, and 40C may be a hole formed inside the protrusion portion 331, for example.

While various embodiments have been described with reference to the drawings, needless to say, the present invention is not limited to such examples. It will be apparent to those skilled in the art that various changes and modifications can be made within the scope of the claims, and it is understood that these are naturally belong within the technical scope of the present invention. Further, each of the components of the above-described embodiments may be combined as desired within a range that does not depart from the spirit of the present invention.

Note that the present application is based on Japanese Patent Application filed on Mar. 27, 2020 (JP 2020-057186), the content of which is incorporated herein by reference.

REFERENCE NUMERALS LIST

1 Wheeze detection device
1 Gripping portion
1*a* Head portion
2 Case
3 Measurement unit
3*a* Pressure receiving unit
4 Integrated control unit
5 Battery
6 Display unit
S Body surface
Ha Hand
30 First housing
33 Second housing
34 O-ring
35 Flexible circuit board
350*a* Through hole
36 Housing cover
37 Case
40 Hole portion
SP1 Accommodation space
M1 First microphone
M2 Second microphone

What is claimed is:

1. A wheeze detection device for detecting wheezing based on a sound measured from a living body while the wheeze detection device is in contact with a body surface of the living body, the wheeze detection device comprising:
   a sound measurement element;
   a space-forming member that forms an accommodation space accommodating the sound measurement element; and
   a cover member that forms a pressure receiving unit that closes the accommodation space and is configured to receive a pressure from the body surface, wherein
   the space-forming member has a hole portion connected to an atmosphere,
   the accommodation space is connected to the atmosphere via the hole portion, and
   the hole portion includes a branch portion between an inlet on a side of the accommodation space and an outlet on a side of the atmosphere and two branched other hole portions branched at the branch portion from a side of the inlet, one branched other hole portion among the two branched other hole portions being connected to the outlet, and the other branched other hole portion among the two branched other hole portions being closed.

2. The wheeze detection device according to claim 1, wherein the hole portion further includes at least one other branch portion in the one branched other hole portion among the two branched other hole portions.

3. The wheeze detection device according to claim 1, wherein
   the space-forming member includes a tubular member and a placement member, the tubular member having one end surface in an axial direction covered with the cover member, and the placement member being fixed to another end surface in the axial direction of the tubular member in a way of closing an inner circumferential portion of the tubular member, wherein the placement member is to place the sound measurement element, and
   the hole portion is configured by a groove formed in the placement member.

4. The wheeze detection device according to claim 2, wherein
   the space-forming member includes a tubular member and a placement member, the tubular member having one end surface in an axial direction covered with the cover member, and the placement member being fixed to another end surface in the axial direction of the tubular member in a way of closing an inner circumferential portion of the tubular member, wherein the placement member is to place the sound measurement element, and
   the hole portion is configured by a groove formed in the placement member.

* * * * *